US008858617B2

(12) United States Patent
Roeder et al.

(10) Patent No.: US 8,858,617 B2
(45) Date of Patent: Oct. 14, 2014

(54) BARBED ANCHORS FOR WIRE STENT (71) Applicant: Cook Medical Technologies LLC, Bloomington, IN (US)

(72) Inventors: Blayne A. Roeder, Bloomington, IN (US); William K. Dierking, Louisville, KY (US); David E. Orr, Piedmont, SC (US); Bent Oehlenschlaeger, Skensved (DK); Erik E. Rasmussen, Slagelse (DK); Julie E. Urbanski, Bloomington, IN (US); Michael W. Hardert, Bloomington, IN (US); Thomas Osborne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/790,855

(22) Filed: Mar. 8, 2013

(65) Prior Publication Data
US 2013/0190858 A1    Jul. 25, 2013

Related U.S. Application Data (62) Division of application No. 12/360,638, filed on Jan. 27, 2009, now Pat. No. 8,394,139.

(60) Provisional application No. 61/093,172, filed on Aug. 29, 2008.

(51) Int. Cl.
A61F 2/848 (2013.01)
A61F 2/06 (2013.01)
A61F 2/86 (2013.01)
A61F 2/07 (2013.01)

(52) U.S. Cl.
CPC ......... *A61F 2/064* (2013.01); *A61F 2220/0016* (2013.01); *A61F 2/07* (2013.01); *A61F 2002/8483* (2013.01); *A61F 2/86* (2013.01)
USPC .......................................... 623/1.36; 623/1.35

(58) Field of Classification Search
CPC ................. A61F 2220/0016; A61F 2002/8483
USPC .............................. 623/1.15, 1.32, 1.35, 1.36
See application file for complete search history.

(56) References Cited

U.S. PATENT DOCUMENTS 5,375,612 A * 12/1994 Cottenceau et al. .......... 128/899
5,800,515 A *  9/1998 Nadal et al. .................. 623/1.15

(Continued)

FOREIGN PATENT DOCUMENTS

EP      0701800 A1   3/1996
WO   WO 00/35352 A1  6/2000

OTHER PUBLICATIONS

Office Action received for corresponding U.S. Appl. No. 12/360,638 dated Apr. 8, 2010 (8 pages).

(Continued)

*Primary Examiner* — Thomas J Sweet
*Assistant Examiner* — Seema Mathew
(74) *Attorney, Agent, or Firm* — Brinks Gilson & Lione (57) ABSTRACT An endoluminal prosthesis that includes a support structure comprising a curvilinear portion having a first strut and a second strut that meet at an apex. Disposed on the support structure is an anchor with an anchor body and one or more barbs extending outwardly from the anchor body and where the anchor body comprises a multi-filar tube fits at least partially about, and conforms to the first strut, second strut, and the apex.

18 Claims, 7 Drawing Sheets

(56) References Cited

U.S. PATENT DOCUMENTS

| | | | | |
|---|---|---|---|---|
| 5,843,164 | A * | 12/1998 | Frantzen et al. | 623/1.16 |
| 5,902,334 | A * | 5/1999 | Dwyer et al. | 606/194 |
| 5,961,546 | A * | 10/1999 | Robinson et al. | 623/1.14 |
| 6,004,347 | A * | 12/1999 | McNamara et al. | 623/23.64 |
| 6,203,568 | B1 | 3/2001 | Lombardi et al. | 623/1.13 |
| 6,214,025 | B1 * | 4/2001 | Thistle et al. | 606/200 |
| 6,231,581 | B1 * | 5/2001 | Shank et al. | 606/157 |
| 6,409,757 | B1 | 6/2002 | Trout, III et al. | 623/1.36 |
| 6,610,085 | B1 * | 8/2003 | Lazarus | 623/1.11 |
| 6,918,921 | B2 * | 7/2005 | Brady et al. | 606/200 |
| 7,527,645 | B2 * | 5/2009 | Perez et al. | 623/1.23 |
| 7,572,289 | B2 | 8/2009 | Sisken et al. | 623/1.36 |
| 7,959,670 | B2 * | 6/2011 | Bolduc | 623/1.36 |
| 8,163,007 | B2 | 4/2012 | Dierking et al. | 623/1.36 |
| 8,696,739 | B2 * | 4/2014 | Dierking et al. | 623/1.36 |
| 2002/0022853 | A1 | 2/2002 | Swanson et al. | 606/155 |
| 2002/0091439 | A1 * | 7/2002 | Baker et al. | 623/1.36 |
| 2003/0144688 | A1 | 7/2003 | Brady et al. | 606/200 |
| 2003/0158604 | A1 | 8/2003 | Cauthen, III et al. | 623/17.16 |
| 2003/0236570 | A1 * | 12/2003 | Cook et al. | 623/1.36 |
| 2004/0117004 | A1 | 6/2004 | Osborne et al. | 623/1.36 |
| 2004/0220595 | A1 | 11/2004 | Frazier et al. | 606/151 |
| 2005/0070993 | A1 | 3/2005 | Boekstegers et al. | 623/1.25 |
| 2005/0080480 | A1 | 4/2005 | Bolea et al. | 623/1.15 |
| 2005/0159803 | A1 * | 7/2005 | Lad et al. | 623/1.13 |
| 2005/0240259 | A1 * | 10/2005 | Sisken et al. | 623/1.36 |
| 2008/0021544 | A1 | 1/2008 | Majercak et al. | 623/1.36 |
| 2008/0033534 | A1 | 2/2008 | Cook et al. | 623/1.36 |
| 2009/0048664 | A1 * | 2/2009 | Cage | 623/1.36 |
| 2009/0149945 | A1 * | 6/2009 | Pike | 623/1.36 |
| 2009/0149946 | A1 * | 6/2009 | Dixon | 623/1.36 |
| 2009/0171442 | A1 * | 7/2009 | Young et al. | 623/1.15 |
| 2010/0130470 | A1 * | 5/2010 | Pauls et al. | 514/211.06 |
| 2010/0312330 | A1 * | 12/2010 | Majercak et al. | 623/1.36 |
| 2011/0118823 | A1 | 5/2011 | Randall et al. | 623/1.36 |
| 2011/0276091 | A1 * | 11/2011 | Melanson et al. | 606/232 |
| 2013/0073029 | A1 * | 3/2013 | Shaw | 623/1.36 |
| 2014/0039602 | A1 * | 2/2014 | Hadley et al. | 623/1.15 |
| 2014/0100512 | A1 * | 4/2014 | Meade et al. | 604/8 |
| 2014/0114400 | A1 * | 4/2014 | McGee et al. | 623/1.36 |

OTHER PUBLICATIONS

Office Action received for corresponding U.S. Appl. No. 12/360,638 dated Jan. 24, 2011 (6 pages).

Office Action received for corresponding U.S. Appl. No. 12/360,638 dated Oct. 14, 2011 (7 pages).

Notice of Panel Decision received for corresponding U.S. Appl. No. 12/360,638 dated Mar. 27, 2012 (2 pages).

Advisory Action received for corresponding U.S. Appl. No. 12/360,638 dated Apr. 12, 2012 (3 pages).

Office Action received for corresponding U.S. Appl. No. 12/360,638 dated May 25, 2012 (5 pages).

* cited by examiner

BARBED ANCHORS FOR WIRE STENT

RELATED APPLICATIONS

The application is a divisional application of U.S. patent application Ser. No. 12/360,638, filed Jan. 27, 2009 which claims the benefit of Provisional U.S. Patent Application Ser. No. 61/093,172, filed Aug. 29, 2008, which is hereby incorporated by reference.

TECHNICAL FIELD

The present invention relates to attachable anchors with barbs for use on a stent and methods of attaching the anchors onto stents.

BACKGROUND

Barbs attached to stents help secure placement of a stent graft in a treated vasculature. Proper stent attachment and placement of the barb ensures that the stent graft will stay in place for the lifespan of the stent graft. Some stent designs limit the barb attachment location and method of attachment due to the material used in the barb and stent and due to the material used to attach the two. Other factors may also limit the barb attachment location, including strut crossover during crimping or potential stent fatigue failure due to weld location near a region on the wire stent of high stress or strain.

Some methods of attaching barbs to wire stents include silver soldering the barb to the wire stent, laser cutting the barb directly into a cannula-cut stent design, and laser welding a barb to the strut of the wire stent. Each of these methods may present particular limitations to barb placement and barb fatigue life depending on the stent design. The industry would benefit from expanded capabilities in barb attachment methods.

BRIEF SUMMARY

Described herein is an endoluminal prosthesis that comprises a support structure having a curvilinear portion and an elongate portion. The curvilinear portion can have a first strut and a second strut that meet at an apex. There is an anchor that has an anchor body and one or more barbs extending outwardly from the anchor body. The anchor body fits at least partially about and conforms to the first strut, the second strut, and the apex.

An anchor can be positioned at or near the apex of the stent. The anchor monolithically can comprise a first end having a barb and a second end. The second end can comprise two or more substantially curved portions configured to fit about a strut of the stent. The second end also can be bifurcated. The bifurcated end can comprise a first substantially curved clamping portion configured to fit about the first strut and a second substantially curved clamping portion configured to fit about the second strut.

The anchor can also be made of a plurality of wires that are arranged in a multi-filar tube. The tube has a first end that is disposed, at least in part, about the first strut and a second end that is disposed, at least in part, about the second strut. The multi-filar tube can conform to a first strut, second strut, or an apex.

The anchor can include a monolithic longitudinal body having a barb at one end and two or more substantially opposing curved portions perpendicular to that longitudinal body. Each curved portion can be configured to fit about and conform to one of the struts of the stent.

Disclosed in this description is an endoluminal prosthesis that has a stent comprising a curvilinear portion and an elongate portion, with the curvilinear portion having at least two struts meeting at an apex, and an anchor on the stent comprising a longitudinal body having a barb at one end and first and second substantially opposing curved portions disposed along the length of, and perpendicular to, the longitudinal body. The first curved portion can be longitudinally offset from the second curved portion and each curved portion can be configured to fit about and conform to a strut.

There is also a method of attaching an anchor to an endoluminal support structure comprising a curvilinear portion having a first strut and a second strut that meet at an apex. The method comprises the steps of arranging a first end of the anchor so that it fits at least partially about, and conforms to, the first strut; arranging a second end of the anchor so that it fits at least partially about, and conforms to, the second strut; and arranging the anchor so that it fits at least partially about, and conforms to, the apex.

An anchor device for an endoluminal prosthesis can include a plurality of independent wires arranged to form a multi-filar tube having a first end, a second end, and a longitudinal axis. One of the wires has an end that forms a first barb that extends outwardly from the anchoring device and acts to contact another prosthesis or a vessel wall. The multi-filar tube can also comprise a second wire with an end that forms a second barb that extends outwardly from the anchoring device.

BRIEF DESCRIPTION OF THE DRAWINGS

FIG. 1b is a perspective view of an anchor made from a stamped out sheet shown in FIG. 1a.

DETAILED DESCRIPTION OF THE DRAWINGS AND THE PRESENTLY PREFERRED EMBODIMENTS

The term "prosthesis" means any replacement for a body part or for a function of that body part or any device that enhances or adds functionality to a physiological system.

The term "support structure" means any device that is attached to a prosthesis. For example, a support structure can comprise stents, radiopaque markers, anchoring stents, barbs, and lateral support rings for supporting a fenestration. The structural components can be attached to the exterior of the graft, the interior of the graft, and/or can be sandwiched between two or more layers of graft material.

The support structure can be made from numerous base materials, such as: biocompatible metals or other metallic materials; polymers including bioabsorbable or biostable polymers; stainless steels; nickel-titanium alloys including shape memory or superelastic types (e.g., nitinol or elastinite); noble metals including platinum, gold, or palladium; refractory metals including tantalum, tungsten, molybdenum, or rhenium; stainless steels alloyed with noble and/or refractory metals; silver; rhodium; inconel; iridium; niobium; titanium; magnesium; amorphous metals; plastically deformable metals (e.g., tantalum); nickel-based alloys (e.g., including platinum, gold, and/or tantalum alloys); iron-based alloys (e.g., including platinum, gold, and/or tantalum alloys); cobalt-based alloys (e.g., including platinum, gold, and/or tantalum alloys); cobalt-chrome alloys (e.g., elgiloy); cobalt-chromium-nickel alloys (e.g., phynox); alloys of cobalt, nickel, chromium, and molybdenum; cobalt-chromium-vanadium alloys; cobalt-chromium-tungsten alloys; platinum-iridium alloys; platinum-tungsten alloys; magnesium alloys; titanium alloys (e.g., TiC, TiN); tantalum alloys (e.g., TaC, TaN); L605; magnetic ferrite; nonmetallic biocompatible materials including polyamides, polyolefins (e.g., polypropylene or polyethylene), nonabsorbable polyesters (e.g., polyethylene terephthalate), or bioabsorbable aliphatic polyesters (e.g., homopolymers or copolymers of lactic acid, glycolic acid, lactide, glycolide, para-dioxanone, trimethylene carbonate or ε-caprolactone); polymeric materials (e.g., poly-L-lactic acid, polycarbonate, polyethylene terephthalate, or engineering plastics such as thermotropic liquid crystal polymers (LCPs)); biocompatible polymeric materials (e.g., cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene, or polytetrafluoroethylene); degradable or biodegradable polymers, plastics, natural (e.g., animal, plant, or microbial) or recombinant material (e.g., polylactic acid, polyglycolic acid, polyanhydride, polycaprolactone, polyhydroxybutyrate valerate, polydepsipeptides, nylon copolymides, conventional poly (amino acid) synthetic polymers, pseudo-poly(amino acids), or aliphatic polyesters (e.g., polyglycolic acid (PGA), poly-lactic acid (PLA), polyalkylene succinates, polyhydroxybutyrate (PHB), polybutylene diglycolate, poly epsilon-caprolactone (PCL), polydihydropyrans, polyphosphazenes, polyorthoesters, polycyanoacrylates, polyanhydrides, polyketals, polyacetals, poly(.alpha.-hydroxy-esters), poly (carbonates), poly(imino-carbonates), poly(.beta.-hydroxy-esters), or polypeptides)); polyethylene terephthalate (e.g., Dacron® or Mylar®); expanded fluoropolymers (e.g., polytetrafluoroethylene (PTFE)); fluorinated ethylene propylene (FEP); copolymers of tetrafluoroethylene (TFE) and per fluoro(propyl vinyl ether) (PFA)); homopolymers of polychlorotrifluoroethylene (PCTFE) and copolymers with TFE; ethylene-chlorotrifluoroethylene (ECTFE); copolymers of ethylene-tetrafluoroethylene (ETFE); polyvinylidene fluoride (PVDF); polyvinyfluoride (PVF); polyaramids (e.g., Kevlar®); polyfluorocarbons including polytetrafluoroethylene with and without copolymerized hexafluoropropylene (e.g., Teflon® or Goretex®); expanded fluorocarbon polymers; polyglycolides; polylactides; polyglycerol sebacate; polyethylene oxide; polybutylene terepthalate; polydioxanones; proteoglymays; glycosaminoglymays; poly(alkylene oxalates); polyalkanotes; polyamides; polyaspartimic acid; polyglutarunic acid polymer; poly-p-diaxanone (e.g., PDS); polyphosphazene; polyurethane including porous or nonporous polyurethanes; poly(glycolide-trimethylene carbonate); terpolymer (copolymers of glycolide, lactide, or dimethyltrimethylene carbonate); polyhydroxyalkanoates (PHA); poly-hydroxybutyrate (PHB) or poly(hydroxybutyrate-co-valerate) (PHB-co-HV); poly(epsilon-caprolactone) (e.g., lactide or glycolide); poly(epsilon-caprolactone-dimethyltrimethylene carbonate); polyglycolic acid (PGA); poly-L and poly-D (lactic acid) (e.g., calcium phosphate glass); lactic acid/ethylene glycol copolymers; polyarylates (L-tyrosine-derived) or free acid polyarylates; polycarbonates (tyrosine or L-tyrosine-derived); poly(ester-amides); poly(propylene fumarate-co-ethylene glycol) copolymer (e.g., fumarate anhydrides); polyanhydride esters; polyanhydrides; polyorthoesters; prolastin or silk-elastin polymers (SELP); calcium phosphate (bioglass); compositions of PLA, PCL, PGA ester; polyphosphazenes; polyamino acids; polysaccharides; polyhydroxyalkanoate polymers; various plastic materials; Teflon®; nylon; block polymers or copolymers; Leica RM2165; Leica RM2155; organic fabrics; biologic agents (e.g., protein, extracellular matrix component, collagen, fibrin); small intestinal submucosa (SIS) (e.g., vacuum formed SIS); collagen or collagen matrices with growth modulators; aliginate; cellulose and ester; dextran; elastin; fibrin; gelatin; hyaluronic acid; hydroxyapatite; polypeptides; proteins; ceramics (e.g., silicon nitride, silicon carbide, zirconia or alumina); bioactive silica-based materials; carbon or carbon fiber; cotton; silk; spider silk; chitin; chitosan (NOCC or NOOC-G); urethanes; glass; silica; sapphire; composites; any mixture, blend, alloy, copolymer or combination of any of these; or various other materials not limited by these examples.

The term "stent" means any device that provides rigidity, expansion force, or support to a prosthesis, such as a stent graft. In one configuration, the stent can represent a plurality of discontinuous devices. In another configuration, the stent can represent one device. Stents can have a wide variety of configurations and can be balloon-expandable or self-expanding. Typically, stents have a circular cross-section when fully expanded, so as to conform to the generally circular cross-section of a body lumen. In one example, a stent can comprise struts (elongate portions) and acute bends (curvilinear portions) that are arranged in a zig-zag configuration, as exemplified in a Z-stent, in which the struts are set at angles to each other and are connected by the acute bends.

A variety of biocompatible materials can be employed to construct the stent, or portions of the stent, including metals and/or alloys, medically-acceptable polymers and/or bioabsorbable polymers, or materials. The metals and/or alloys may, among other things, include stainless steel, tantalum, nitinol, gold, silver, tungsten, platinum, inconel, cobalt-chromium alloys, and iridium, all of which are commercially available metals or alloys used in the fabrication of medical devices. In a preferred configuration, the stent is constructed from nitinol, stainless steel, and/or cobalt-chromium alloys.

The anchors having barbs described herein can be in one piece, or monolithic, or have multiple wires in a multi-filar configuration to form a tube. The monolithic anchors can be stamped, machined, or laser cut out of a sheet of biocompatible material. The multi-filar anchors can be provided with wires having circular or polygonal cross-sections by methods used in the art.

Figure 1A:
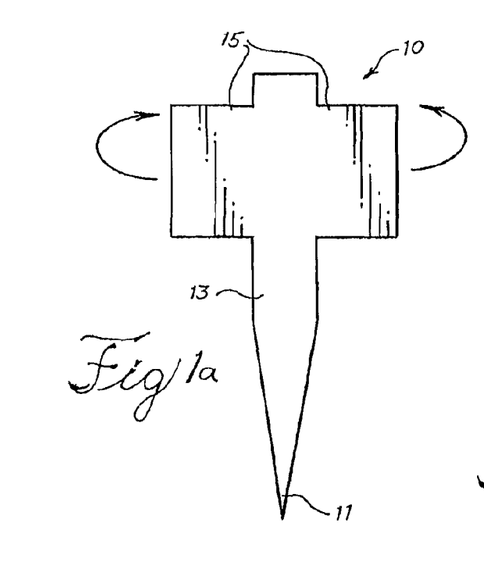
FIG. 1a is a top view of a stamped out sheet of biocompatible material for use as an anchor with two winged portions.
Figure 1B:
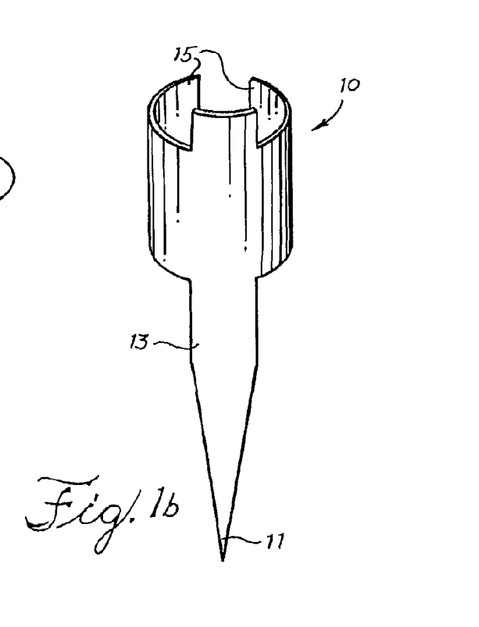
Figure 1C:
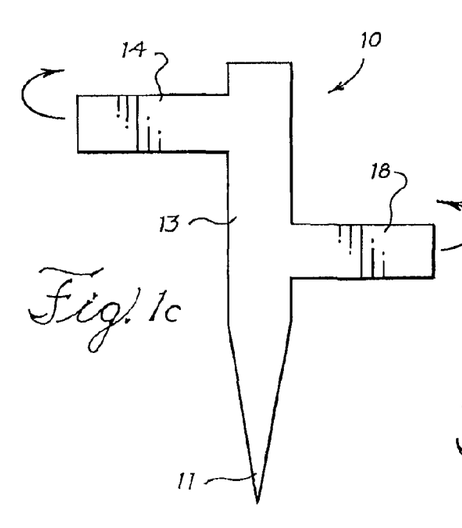
FIG. 1c is a top view of a stamped out sheet of biocompatible material with opposing and off-setting winged segments.
Figure 1D:
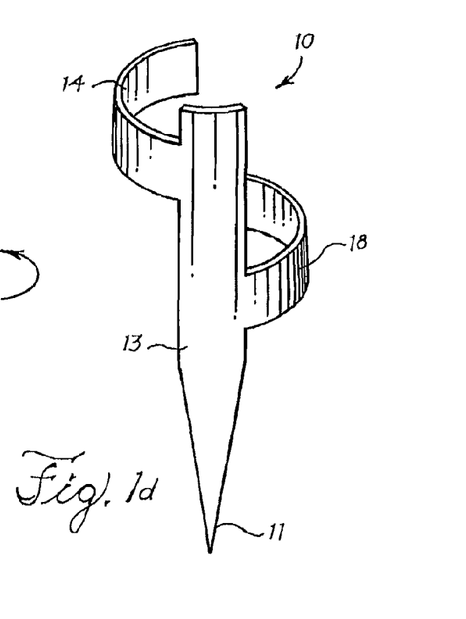
FIG. 1d is a perspective view of an anchor made from the stamped out sheet shown in FIG. 1c.

In FIGS. 1a, 1b, 1c, 1d, 1e, and 1f, the anchor is monolithically constructed. The anchor 10 can include a longitudinal body 13 having a barb 11 at one end and first and second substantially opposing curved portions 15 disposed along the length of, and perpendicular to the longitudinal body 13. In FIG. 1c, the anchor 10 has two substantially opposing portions 15 perpendicular to the longitudinal body 13. These portions 15 will be shaped to fit about and to conform to a strut. In FIG. 1d, an anchor is shown having more than two opposing portion where there is a first curved portion 14 that is longitudinally offset from the second curved portion 18. The curved portions 15 are configured for fastening the anchor 10 to the stent by snap fitting the portions 15 around a strut or, if necessary, soldering the portion 15 to the strut. The anchor also can include a longitudinal body 13 with more than one barb 11. The barb can be forked at the end to provide two or three separate prongs.

The straight portions 15 shown in FIG. 1a are bent in the direction shown by the arrows to provide the two curved portions 15 shown in FIG. 1b. FIG. 1c shows a monolithic anchor 10 with two substantially opposing portions 14, 18 that are longitudinally offset to one another. As shown in FIG. 1d, these portions 14, 18 are manipulated in the direction shown by the arrows to provide two curved portions 14, 18 that conform to the tubular elongate portion of a stent strut.

Figures 1E, 1F:
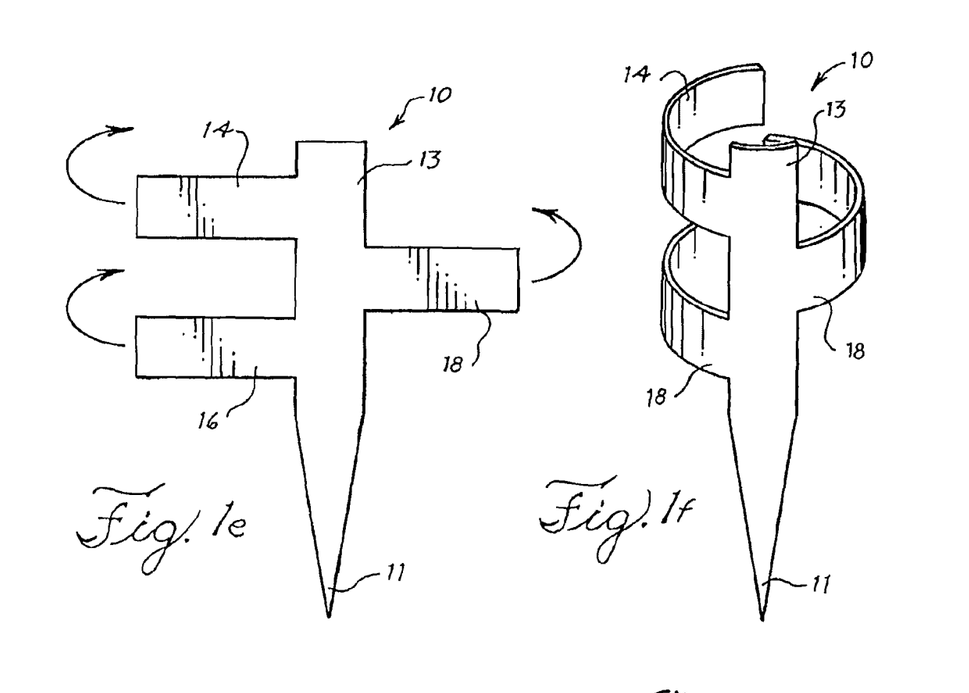
FIG. 1e is a top view of a stamped out sheet of biocompatible material with two winged segments opposed to one winged segment.
FIG. 1f is a perspective view of an anchor made from the stamped out sheet shown in FIG. 1e.

FIG. 1e also shows an anchor 10 formed out of a sheet of biocompatible material. Three portions 14, 16, 18 are bent in the direction shown by the arrows to provide the curved portions 14, 16, 18 shown in FIG. 1f. Curved portions 14, 16, 18 are disposed along the length of and are perpendicular to the longitudinal body 13. Curved portion 18 is longitudinally offset from curved portions 14, 16. An anchor can be made having more than one, two, or even three curved portions where some of the curved portions are opposed to the remainder. The number of curved portions and their configuration can vary. Positioning the curved portions in opposing configurations facilitates the stable attachment of the anchor to the strut of the stent.

Figure 2:
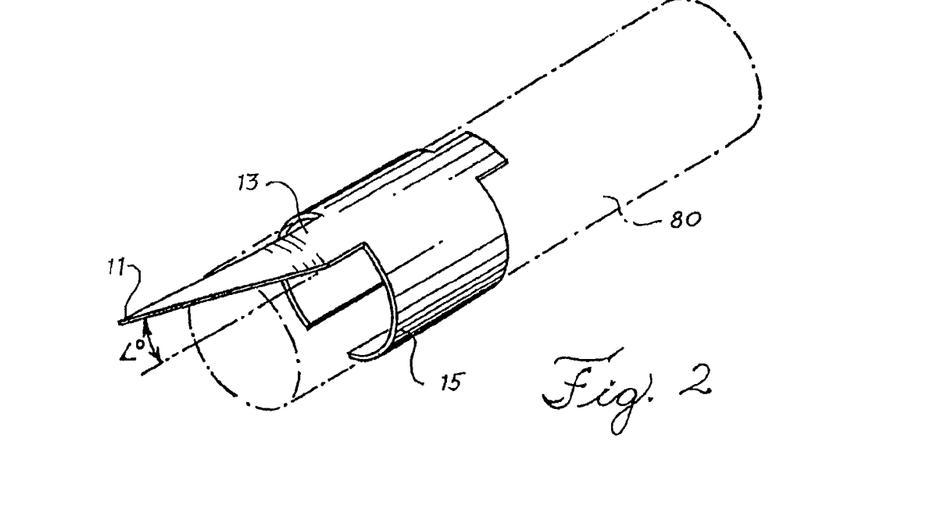
FIG. 2 is a perspective view of an anchor fastened to a stent strut.
Figure 3A:
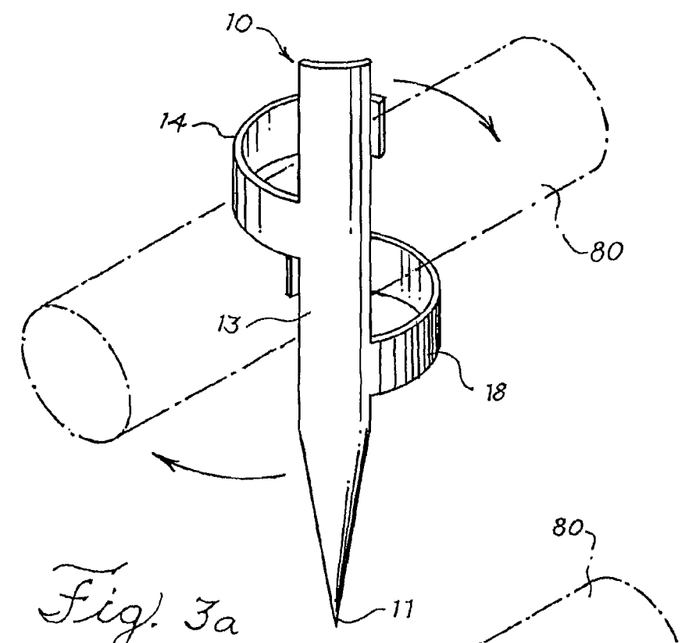
FIGS. 3a and 3b depict the steps to fasten a monolithic anchor to a stent strut.
Figure 3B:
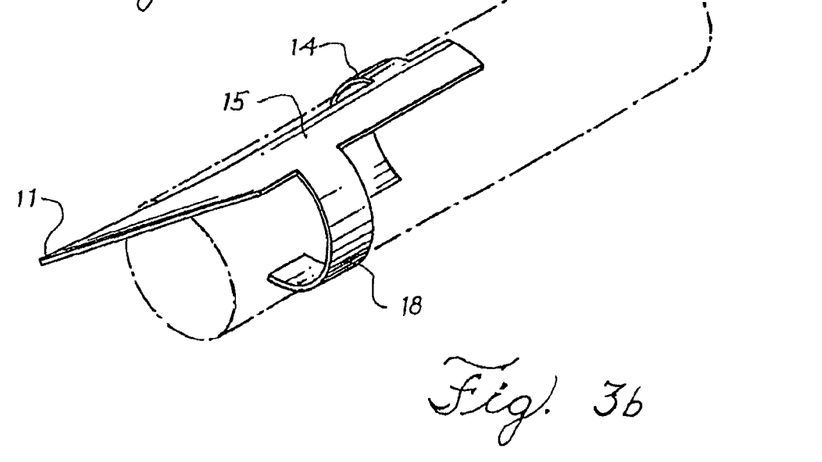

The anchor 10 also includes a barb 11 that, when the prosthesis is implanted into a vasculature, assists in securing the anchor and the stent graft to the vessel wall or to the wall of a mating graft. The barb 11 can be parallel to the elongate portion of a stent strut 80, extend from the elongate portion at an angle away from the strut 80, as shown in FIG. 2, or bent towards the strut 80. The barb 11 in FIG. 3b is in line with the stent elongate portion 80.

Figure 5A:
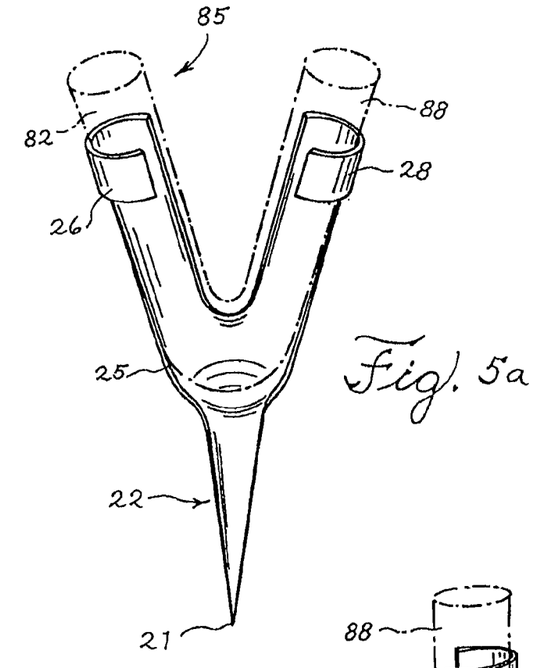
FIG. 5a is a perspective view of a monolithic anchor with a bifurcated attachment end fastened to a curvilinear portion of a stent strut.

The anchor 10 can have geometries permitting press-fit or snap-on placement of the anchor 10 onto a stent strut at either an elongate 80 portion or at the curvilinear 85, or apex, portion of a Z-stent, as shown in FIG. 5a. A sheet of an appropriate material, such as an alloy, can be stamped to incorporate curved and linear segments that act to fasten the anchor 10 around the stent strut 80 and hold the anchor 10 in place. FIG. 2 shows an anchor 10 fastened to the elongate portion 80 of a stent. FIG. 5a shows an anchor 20 fastened to the curvilinear portion 85 of a stent. As shown in FIG. 5, the two clamping portions 26, 28 of the anchor substantially mimic and conform to the curvilinear portion 85 of the stent. The clamping portions 26, 28 of the anchor 10 then can support the resultant forces and moments through the points of contact between the stent and the anchor 10 without the need for solder, welding, glue, or epoxy.

There is a method of attaching an anchor 10 to an endoluminal support structure that has an elongate strut 80. FIGS. 3a and 3b are illustrations of steps that can be taken to fasten a monolithic anchor 10 having two offset curved portions 14, 18 to the elongate strut 80. The two curved portions 14, 18 are offset and opposed to one another and are bent to fit around the stent elongate portion 80. To fasten the anchor 10 onto the stent elongate portion 80 the, the longitudinal body 13 part of the anchor 10 is initially placed perpendicular to the stent elongate portion 80 such that the elongate portion 80 lies between the curved portions 14, 18. The anchor 10 can then be rotated in a clockwise direction as shown by the arrows in FIG. 3a to fasten the anchor 10 to the elongate portion 80. As shown in FIG. 3b, rotating the anchor 10 so that the longitudinal body 13 is in line with the elongate portion 80 of the stent strut can snap the curved portions 14, 18 around the stent strut, thus attaching the anchor 10 to the stent.

An anchor can be provided such that it is fastened to the elongate portion 80 by turning the anchor 10 in a counter-clockwise direction. The curved portions 14, 18 also can be provided such that the longitudinal body 13 of the anchor 10 contacts the elongate portion and then adjusted turned 45 degrees to fit onto the elongate portion 80.

Figure 4:
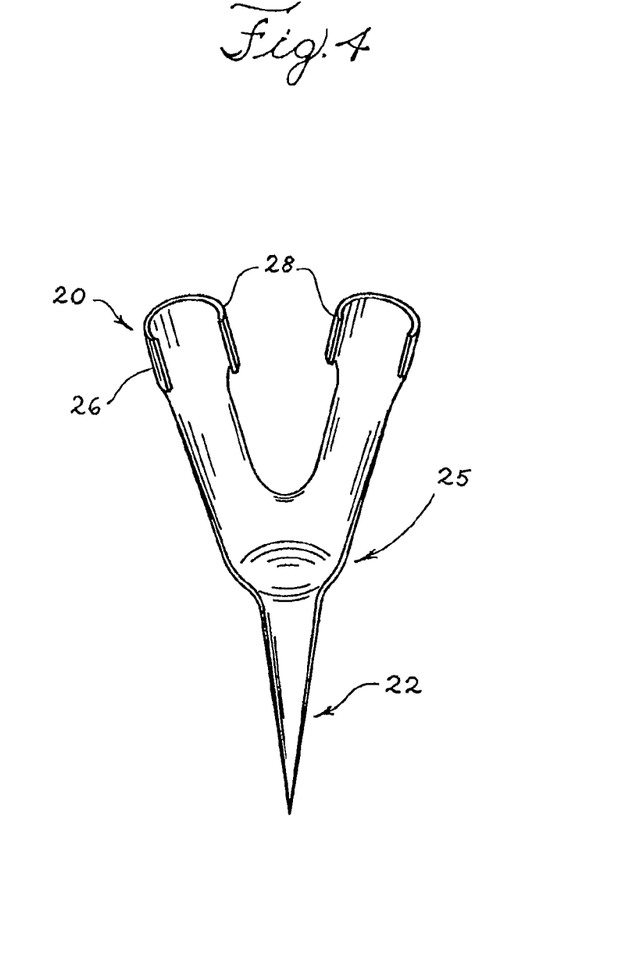
FIG. 4 is a perspective view of a monolithic anchor with a bifurcated end.

As shown in FIG. 5a, an endoluminal prosthesis can include a support structure comprising a curvilinear portion 85 having a first strut 82 and a second strut 88 meeting at an apex 83. The prosthesis also can include an anchor 20 comprising an anchor body and one or more barbs 21 extending outwardly from the anchor body. The anchor body fits at least partially about, and conforms to, the first strut 82, the second strut 88, and the apex 83. In FIG. 4, the anchor has a longitudinal structure with a first end 22 with a barb 21 and a second, bifurcated end 25. The second end 25 includes a first substantially curved clamping portion 26 configured to fit about the first strut 82 and a second substantially curved clamping portion 28 configured to fit about the second strut 88.

FIG. 5a shows a stent curvilinear portion 85 in dashed lines along with the first 82 and second 88 struts meeting at an apex 83. The apex 83 points in one direction and when an anchor 20 is attached, the barb 21 can extend in that one direction. The barb 21 also can be bent at an angle or in a different direction than the apex 83.

The second, bifurcated end 25 includes two substantially curved clamping portions 26, 28 that can be configured to fit about the two struts found on the curvilinear portion of a stent. The two substantially curved clamping portions 26, 28 can be designed for press-fit or snap-on placement onto the stent. The two substantially curved clamping portions 26, 28 also can be soldered onto the stent struts.

Figure 5B:
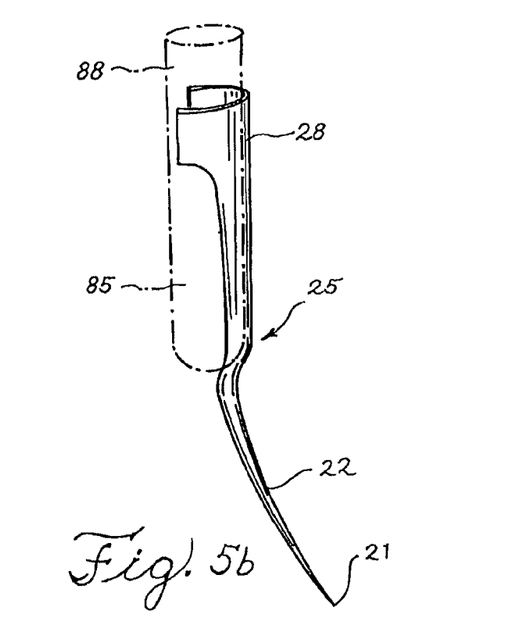
FIG. 5b is a profile view of a monolithic anchor with a bifurcated attachment end fastened to a curvilinear portion of a stent strut.

FIGS. 5a and 5b show the anchor 20 fastened to the curvilinear portion 85 from the front (FIG. 5a) and from a profile view (FIG. 5b). The barb 21 can contact an endoluminal wall when implanted into a vessel. The anchor 20 in FIG. 5b has a barb 21 that is bent at an angle where the barb 21 is pointing away from where the stent graft (not shown) is positioned. The barb 21 also can be in line with the apex 83 as seen in FIG. 5a or be bent laterally in a variety of directions.

An anchor can be attached to the endoluminal support structure that has a curvilinear portion with a first strut and a second strut meeting at an apex. The method of attachment can include arranging a first end of the anchor so that it fits at least partially about, and conforms to, the first strut. A second end of the anchor is arranged so that it fits at least partially about, and conforms to, the second strut. The anchor can also be arranged so that it fits at least partially about, and conforms to, the apex. The anchor can be arranged such that it is snapped to the first strut, the second strut, and the apex of the curvilinear portion of a stent.

Figures 6, 7:
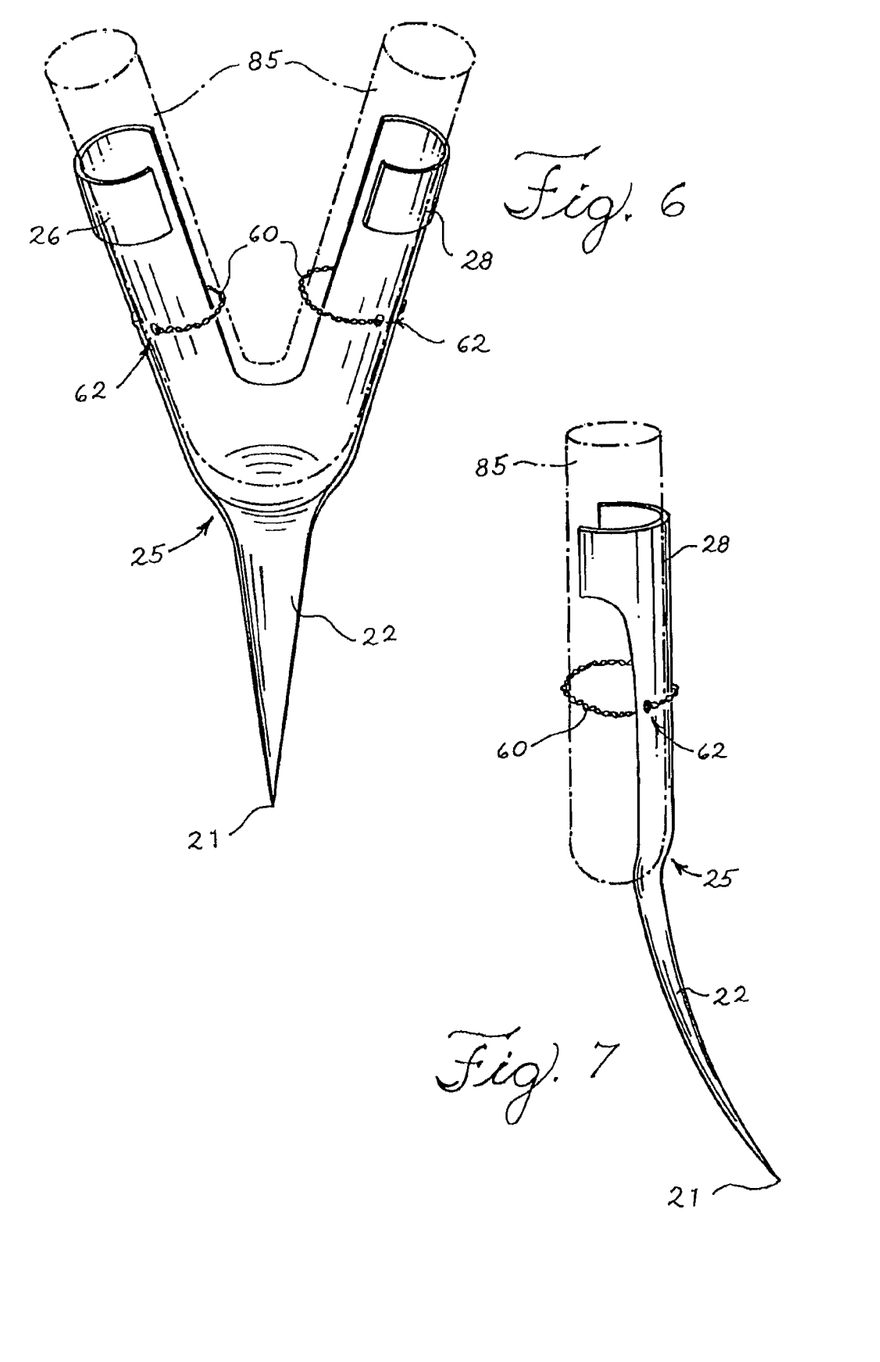
FIG. 6 is a perspective view of a monolithic anchor with a bifurcated attachment end fastened to a curvilinear portion of a stent strut with support sutures.
FIG. 7 is a profile view of an anchor fastened to a stent strut with support sutures.

Additionally, support sutures 60 can be used to fasten the anchor 20 to a stent. FIG. 6 shows an anchor 20 with a second bifurcated end 25 with openings 62 in the substantially curved clamping portions 26, 28 through which support sutures 60 can be threaded. FIG. 7 is a profile view of an anchor 20 having support sutures 60 threaded around the curvilinear portion 85, through the openings 62, and around the second curved portion 28. The support sutures 60 can be threaded at least partially around the first 26 and second 28 substantially curved clamping portion.

Figures 8A, 8B:
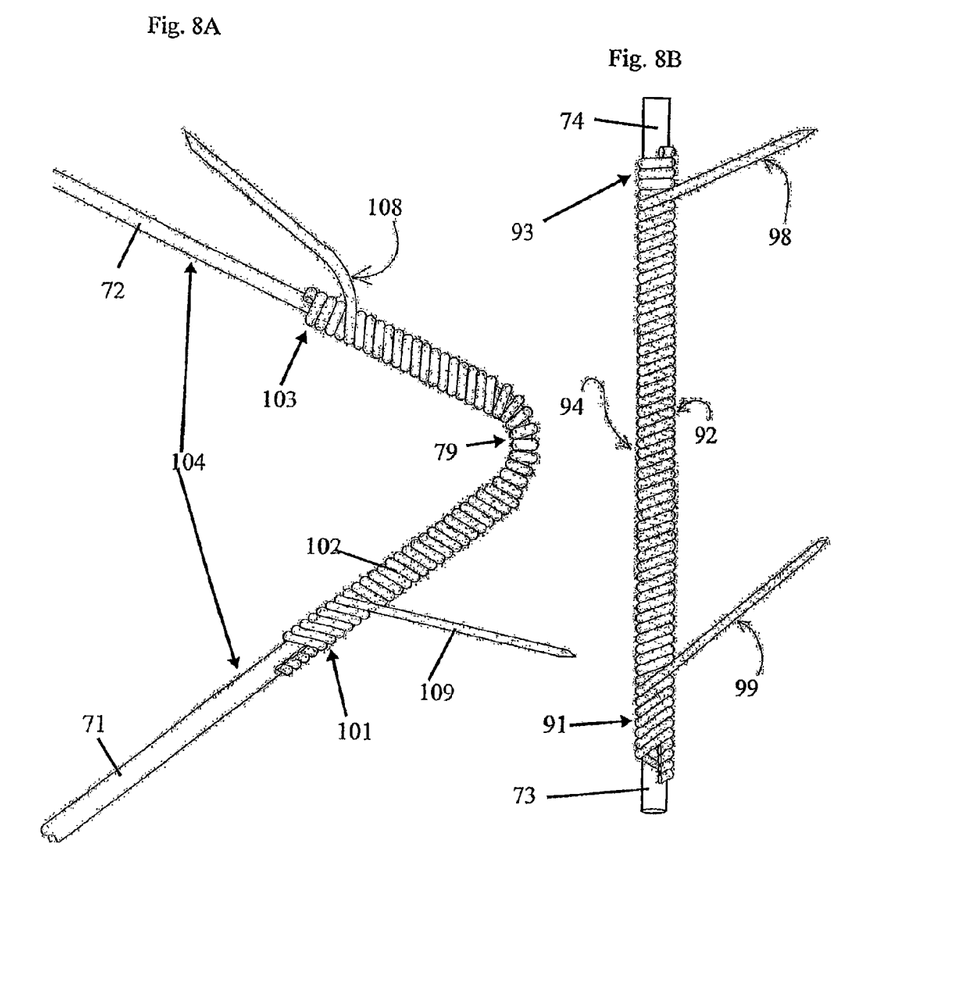
FIG. 8a is a profile view of a multi-filar anchor attached to a curvilinear stent strut.
FIG. 8b are profile view of a multi-filar anchor attached to an elongate strut.

FIGS. 8a and 8b show anchors 102 and 92 attached to curvilinear 104 and elongate 94 stent struts. Anchors 102 and 92 are made of a plurality of independent wires arranged in a multi-filar tube having a first end, a second end and a longitudinal axis. In multi-filar anchors, one of the wires has an end that exits the multi-filar tube and forms a first barb that extends outwardly from the anchoring device. In FIGS. 8a and 8b, the wires are coiled around stent struts 104, 94 to form the multi-filar tubes. The anchors 102, 92 resemble a coil or barbed wire configuration. The wires can have a circular cross-section or a polygonal cross-section. In FIG. 8a, the tube has a first end 101 disposed, at least in part, about the first strut 71 and a second end 103 disposed, at least in part, about the second strut 72. The tube is also disposed around the apex 79 of the curvilinear stent 104 strut. In FIG. 8b, the multi-filar anchor 92 is disposed on an elongate stent strut 94 from the first end 73 to the second end 74 of the stent. The multi-filar anchors have wires wherein each of the wires have a first end disposed at or near the first end of the multi-filar tube and a second end disposed at or near the second end of the multi-filar tube.

At least one wire in the multi-filar anchor has an end that forms at least one barb. In FIGS. 8a and 8b, the multi-filar anchors 102, 92 have barbs 108, 109, 98, 99 formed from the sharpened ends of corresponding wires. Barb 108, which extends outwardly from the anchor 102, is formed from a first wire having an end. There is also a second wire that has an end that forms a second barb 108 that extends outwardly from anchor 102. Similarly, in FIG. 8b, the anchor 92 attached to the elongate strut 94 has a first end 91 that has a barb 99 disposed thereon and a second end 93 with a barb 98 disposed thereon. It is appreciated that a multi-filar anchor similar to that shown in FIG. 8a can be attached to a Z-stent. A multi-filar anchor similar to that show in FIG. 8b can be attached to other interconnected support structures or stents.

When attaching the multi-filar anchor 102, at least a portion of the anchor can be threaded around the first strut 71, the second strut 72, and the apex 79 of the curvilinear stent 104 strut. Similarly, as shown in FIG. 8b, anchor 94 can be threaded around an elongate stent strut 94.

An anchor can be attached to the support structure in a position fixed longitudinally and rotationally. Although some incidental movement can be allowed, the anchor can be attached and fixed such that it will not move substantially longitudinally along a stent or rotate about the stent. The attachment is such that there can be little or no movement by the anchor independent of the stent structure. With monolithic anchors having bifurcated attachment ends, there can be little or no longitudinal or rotational movement. The anchor can be fastened to the stent by laser weld, adhesive, soldering, or friction fit. The anchor can also include nitinol. The substantially curved clamping portions can include nitinol. The nitinol clamping portions can be configured to constrict around a stent strut and provide a secure attachment between the anchor and the stent.

It is therefore intended that the foregoing detailed description be regarded as illustrative rather than limiting, and that it be understood that it is the following claims, including all equivalents, that are intended to define the spirit and scope of this invention.

The invention claimed is:

1. An anchoring device in combination with a stent for an endoluminal prosthesis comprising:
    a plurality of independent wires arranged to form a multi-filar tube having a first tube section, a second tube section, a third tube section between the first and second tube sections, a first end and a second end,
    where each wire of the plurality of wires has a first end and a second end,
    where at least one end of a first wire forms a first barb that extends outwardly from a tube section of the anchoring device,
    where the stent has a first strut, a second strut and an apex between the first and second struts; and
    where the tube sections comprise a coil, and the first tube section is wound about the first strut, the second tube section is wound about the second strut, and the third tube section is wound about the apex.

2. The device of claim 1, where the tube sections comprise at least one coil of the wires.

3. The device of claim 1, where a second wire has an end that forms a second barb that extends outwardly from a tube section of the anchoring device.

4. The device of claim 3, where the first wire end extends from the first tube section, and the second wire extends from the second tube section.

5. The device of claim 1, where the first barb is disposed at or near the first end of the multi-filar tube.

6. The device of claim 5, where at least one end of a second wire forms a second barb that extends outwardly from a tube section of the anchoring device.

7. The device of claim 6, where the second barb is disposed at or near the second end of the multi-filar tube.

8. The device of claim 1, where the first end of the first wire forms the first barb, and the second end of the first wire forms a second barb.

9. The device of claim 8, where the first barb is disposed at or near the first end of the multi-filar tube, and the second barb is disposed at or near the second end of the multi-filar tube.

10. An endoluminal prosthesis comprising:
    a support structure having an apex, and first and second struts meeting at the apex,
    an anchor comprising an anchor body and one or more barbs extending outwardly from the anchor body,
    where the anchor body comprises a multi-filar tube having a first end and a second, end and, where the multi-filar tube comprises a coil that is wound about and conforms to, the first strut, the second strut, and the apex.

11. The endoluminal prosthesis of claim 10, where the multi-filar tube comprises a plurality of independent wires, where each wire of the plurality of wires has a first end and a second end.

12. The endoluminal prosthesis of claim 11, where at least one end of a first wire forms a first barb that extends outwardly from the anchor body.

13. The endoluminal prosthesis of claim 12, where at least one end of a second wire forms a second barb that extends outwardly from the anchor body.

14. The endoluminal prosthesis of claim 13, where the first end of the first wire forms the first barb and the second end of a second wire forms the second barb.

15. The endoluminal prosthesis of claim 12, where the first barb is disposed at or near the first end of the multi-filar tube.

16. The endoluminal prosthesis of claim 14, where the first barb is disposed at or near the first end of the multi-filar tube and the second barb is disposed at or near the second end of the multi-filar tube.

17. The endoluminal prosthesis of claim 12, where a first end of the first wire forms the first barb and a second end of the first wire forms a second barb.

18. The endoluminal prosthesis of claim 17, where the first barb is disposed at or near the first end of the multi-filar tube and the second barb is disposed at or near the second end of the multi-filar tube.

* * * * *